United States Patent
Higuchi

(10) Patent No.: US 11,555,773 B2
(45) Date of Patent: Jan. 17, 2023

(54) INFLAMMATORY MARKER MEASUREMENT METHOD, INFLAMMATORY MARKER MEASUREMENT APPARATUS, INFLAMMATORY MARKER MEASUREMENT PROGRAM, AND RECORDING MEDIUM STORING THE PROGRAM

(71) Applicant: NIHON KOHDEN CORPORATION, Tokyo (JP)

(72) Inventor: Makoto Higuchi, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 749 days.

(21) Appl. No.: 16/469,261

(22) PCT Filed: Jan. 25, 2018

(86) PCT No.: PCT/JP2018/002311
§ 371 (c)(1),
(2) Date: Jun. 13, 2019

(87) PCT Pub. No.: WO2018/139546
PCT Pub. Date: Aug. 2, 2018

(65) Prior Publication Data
US 2020/0018677 A1    Jan. 16, 2020

(30) Foreign Application Priority Data

Jan. 27, 2017 (JP) .............................. JP2017-013292
Oct. 5, 2017 (JP) .............................. JP2017-195393

(51) Int. Cl.
*G01N 15/06* (2006.01)
*G01N 33/49* (2006.01)
(Continued)

(52) U.S. Cl.
CPC ............. *G01N 15/06* (2013.01); *G01N 33/49* (2013.01); *G01N 2015/0073* (2013.01);
(Continued)

(58) Field of Classification Search
CPC ................... G01N 15/06; G01N 33/49; G01N 2015/0073; G01N 2015/055; G01N 2015/0693; G01N 2800/7095
See application file for complete search history.

(56) References Cited

U.S. PATENT DOCUMENTS 5,506,145 A     4/1996 Bull et al.
2009/0311736 A1 * 12/2009 Ciotti ..................... G01N 15/05
                                                              435/29
(Continued)

FOREIGN PATENT DOCUMENTS

CN          1123914 A        6/1996
CN        104931398 A        9/2015
(Continued)

OTHER PUBLICATIONS

Xiaotian Gang, translated by Yunpeng Wu, et al., Biorheology, Science Press, p. 125-147, Dec. 31, 1988.
(Continued)

*Primary Examiner* — Jamil Ahmed
(74) *Attorney, Agent, or Firm* — Pearne & Gordon LLP

(57) ABSTRACT

An inflammatory marker is calculated using a nonlinear function including, as variables, a parameter associated with an erythrocyte aggregation and another parameter associated with an erythrocyte density. The parameter associated with the erythrocyte aggregation is calculated based on a syllectogram measured from a blood specimen. The parameter associated with the erythrocyte density is measured from the blood specimen.

15 Claims, 12 Drawing Sheets

(51) Int. Cl.
*G01N 15/00* (2006.01)
*G01N 15/05* (2006.01)

(52) U.S. Cl.
CPC ........... *G01N 2015/0092* (2013.01); *G01N 2015/055* (2013.01); *G01N 2015/0693* (2013.01); *G01N 2800/7095* (2013.01)

(56) References Cited

U.S. PATENT DOCUMENTS

2014/0315240 A1  10/2014  Dayel et al.
2015/0268221 A1*  9/2015  Fukuda ............... G01N 35/10
                                                      73/61.43

FOREIGN PATENT DOCUMENTS

| WO | 2007-128684 A1 | 11/2007 |
| WO | 2008-006897 A1 | 1/2008 |
| WO | 2011-101815 A1 | 8/2011 |

OTHER PUBLICATIONS

Chinese Office Action dated Mar. 2, 2022 issued in Chinese Patent Application No. 201880009050.2.

Baskurta, Oguz K., et al., "Measurement of red blood cell aggregation in disposable capillary tubes", Clinical Hemorheology and Microcirculation, vol. 47, No. 4, (2011), pp. 295-305.

Chinese Office Action dated Aug. 16, 2021 issued in Patent Application No. 201880009050.2.

Cha, Choong-Hwan, et al., "Evaluation of the TEST 1 erythrocyte sedimentation rate system and intra-and inter-laboratory quality control using new latex control materials", Clin Chem Lab Med 2010; 48(7); pp. 1043-1048, 2010, New York.

Dobbe, Johannes, G. G., et al. "Syllectometry: The Effect of Aggregometer Geometry in the Assessment of Red Blood Cell Shape Recovery and Aggregation", IEEE Transactions on Biomedical Engineering, vol. 50, No. 1, Jan. 2003, pp. 97-107.

International Search Report Issued in Patent Application No. PCT/JP2018/002311 dated Apr. 30, 2018.

Ong, Peng Kai, et al., "Study of Time-Dependent Characteristics of a Syllectogram in the Presence of Aggregation Inhibition", International Journal of Precision Engineering and Manufacturing, vol. 13, No. 3, pp. 421-428, Mar. 2012.

Pribush, A, et al., "A novel approach for assessments of erythrocyte sedimentation rate", International Journal of Laboratory Hematology, 2011, Blackwell Publishing Ltd., vol. 33, pp. 251-257.

Written Opinion Issued in Patent Application No. PCT/JP2018/002311 dated Apr. 30, 2018.

Written Opinion of the International Preliminary Examining Authority issued in Patent Application No. PCT/JP2018/002311 dated Jan. 11, 2019.

Zhbanov, Alexander, et al., "Effects of Aggregation on Blood Sedimentation and Conductivity", PLOS One, DOI: 10.1371, Jun. 5, 2015, pp. 1-25.

* cited by examiner

INFLAMMATORY MARKER MEASUREMENT METHOD, INFLAMMATORY MARKER MEASUREMENT APPARATUS, INFLAMMATORY MARKER MEASUREMENT PROGRAM, AND RECORDING MEDIUM STORING THE PROGRAM

TECHNICAL FIELD

The presently disclosed subject matter relates to an inflammatory marker measurement method, an inflammatory marker measurement apparatus, an inflammatory marker measurement program, and a recording medium storing the program.

BACKGROUND ART

Screening for inflammatory diseases can be performed based on an erythrocyte sedimentation rate (ESR). The Westergren method is the reference method for measuring the ESR. According to the Westergren method, the ESR is measured by reading how many millimeters the interface between sedimenting erythrocytes and the plasma layer remaining on an upper side has shifted down in one hour after transferring collected blood to a sedimentation tube.

Before the erythrocyte sedimentation is observed, aggregation reaction due to erythrocyte rouleaux formation (hereinafter, "erythrocyte aggregation") is observed. This erythrocyte aggregation is facilitated when fibrinogen, which is an inflammatory protein and also a blood coagulation factor, increases in the blood. With a capillary photometry method, the ESR is calculated from an optical density change caused by the erythrocyte aggregation, enabling the ESR measurement in a short period of time of about one minute.

It is said that an ESR value measured by the Westergren method, i.e., the reference method, is relatively largely affected by the hematocrit value which indicates the volume percentage of blood cells in blood. To obtain an ESR measurement value that correctly reflects the degree of inflammation, therefore, a hematocrit-based correction formula may be used.

By contrast, it is said that an ESR value measured by the capillary photometry method is less affected by the hematocrit value, posing a relatively large discrepancy between the ESR value measured by the capillary photometry method and the ESR value measured by the reference method. One reason of this is the hindered settling, that is, the sedimentation rate of particles is lowered as the density of the particles becomes greater. Another reason is that, in the capillary photometry method, the effect of the hindered settling that depends on the hematocrit level is not considered for the sedimentation stage subsequent to the erythrocyte aggregation.

A related study compares the capillary photometry method and the Westergren method, with a correction based on a hematocrit value using the Fabry formula. See, Evaluation of the TEST 1 erythrocyte sedimentation rate system and intra- and inter-laboratory quality control using new latex control materials (Clin Chem Lab Med 2010; 48(7): 1043-1048).

However, even with the correction using the Fabry formula described in the related study, there is still a large discrepancy between an ESR value measured by the capillary photometry method and an ESR value measured by the reference method.

There is a method for measuring the fibrinogen, known as the Clauss method (thrombin time method) in which a high concentration of thrombin is added to diluted citrated blood plasma, and the fibrinogen concentration is obtained based on the time until the fibrinogen is converted to fibrin.

This Clauss method requires complex operations including the separation of plasma, the dilution of plasma, and the addition of thrombin reagent.

SUMMARY OF INVENTION

The presently disclosed subject matter provides a method in which deviation from the reference method or the Clauss method is small, and which measures an inflammatory marker easily and in a short period of time.

According to an aspect of the presently disclosed subject matter, an inflammatory marker measurement method includes calculating an inflammatory marker using a non-linear function having, as variables, a parameter associated with an erythrocyte aggregation and another parameter associated with an erythrocyte density. The parameter associated with the erythrocyte aggregation is calculated based on a syllectogram measured from a blood specimen. The parameter associated with the erythrocyte density is measured from the blood specimen. The inflammatory marker to be calculated may be at least one of an erythrocyte sedimentation rate and a fibrinogen concentration.

DESCRIPTION OF EMBODIMENTS

Figure 1:
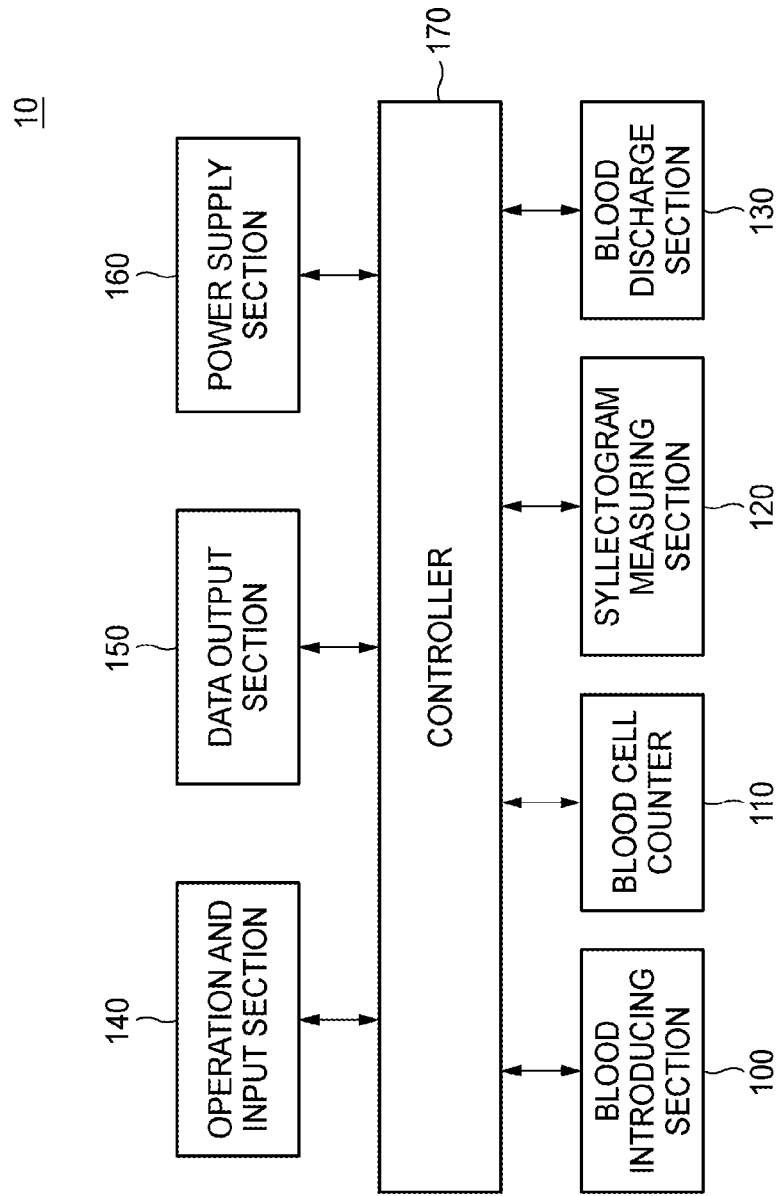
FIG. 1 is a block diagram illustrating a configuration of an inflammatory marker measurement apparatus.

Hereinafter, an inflammatory marker measurement method, an inflammatory marker measurement apparatus, an inflammatory marker measurement program, and a recording medium storing the program according to embodiments of the presently disclosed subject matter will be described in detail with reference to the drawings. In the drawings, the same or similar elements are denoted by the same reference numerals. In the drawings, the dimensional ratio may be exaggerated and may not be to scale for illustrative purpose.

Figure 2:
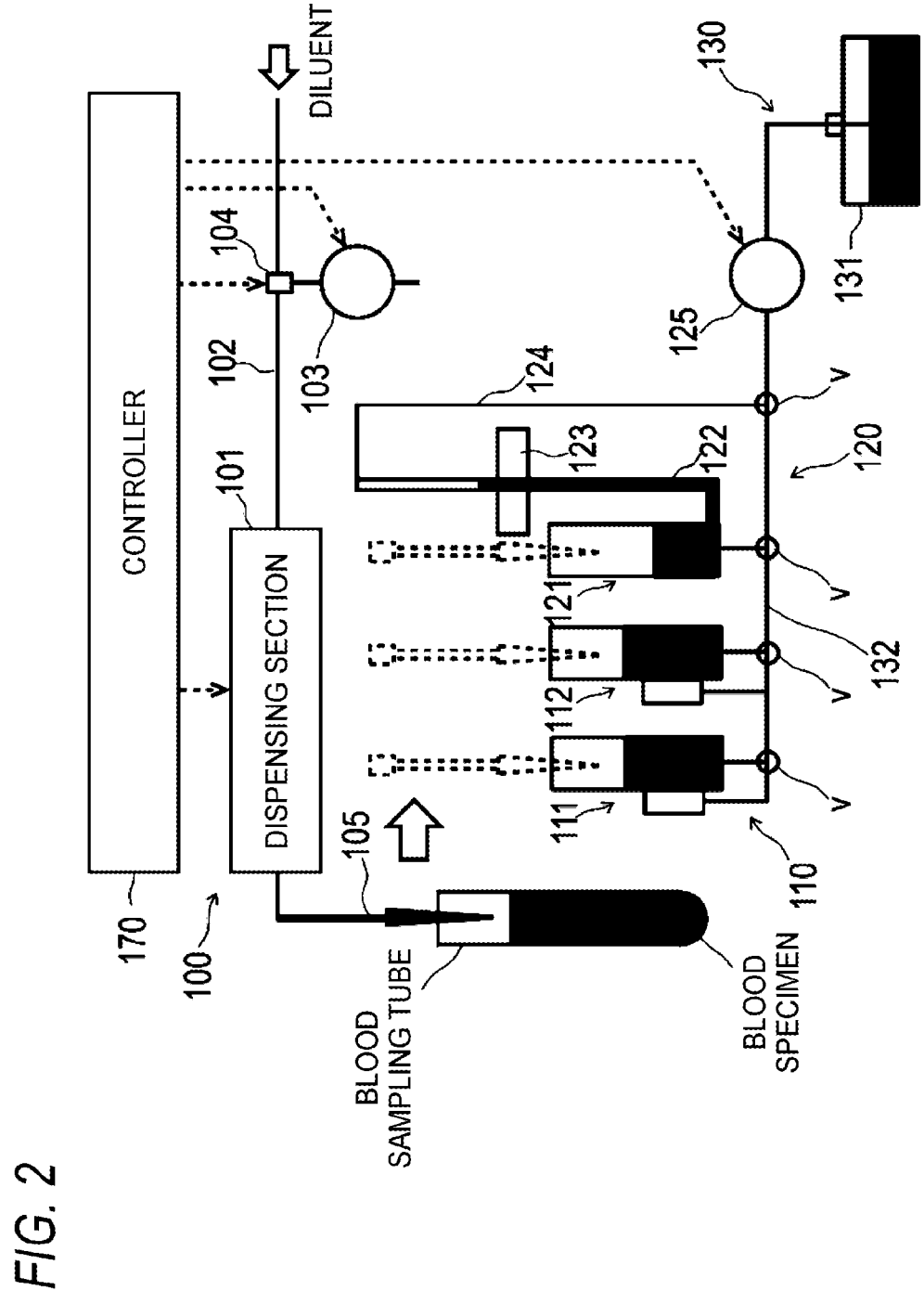
FIG. 2 is a diagram schematically illustrating the inflammatory marker measurement apparatus.
Figure 3:
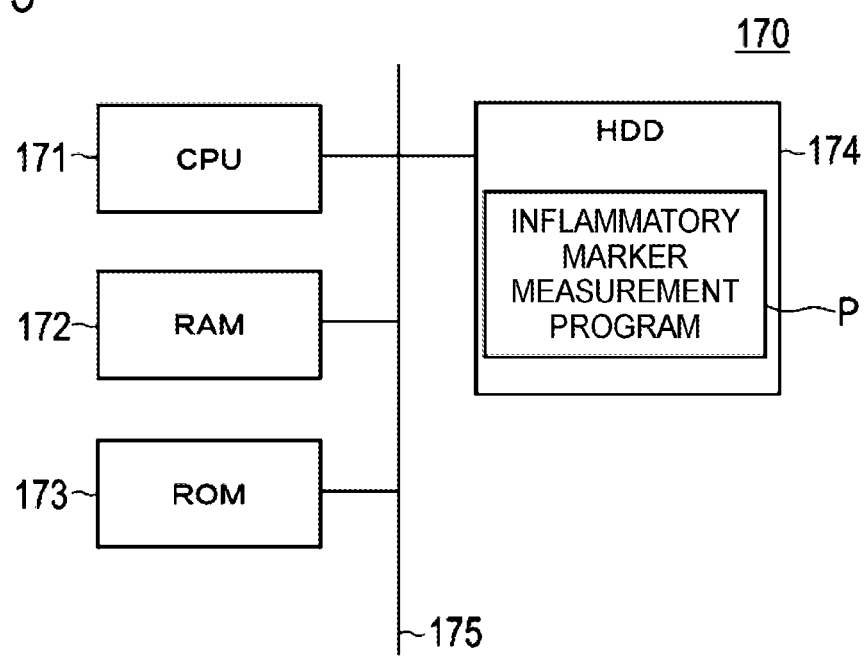
FIG. 3 is a block diagram illustrating a configuration of a controller of the inflammatory marker measurement apparatus.

FIG. 1 is a block diagram illustrating a configuration of an inflammatory marker measurement apparatus according to an embodiment of the presently disclosed subject matter, FIG. 2 is a diagram schematically illustrating the inflammatory marker measurement apparatus, and FIG. 3 is a block diagram illustrating a configuration of a controller of the inflammatory marker measurement apparatus.

Examples of inflammatory marker include an ESR and a fibrinogen concentration. In the present embodiment, the ESR is measured as an inflammatory marker.

The inflammatory marker measurement apparatus 10 has a blood introducing section 100, a blood cell counter 110, a syllectogram measuring section 120, a blood discharge section 130, an operation and input section 140, a data output section 150, a power supply section 160, and the controller 170. The blood introducing section 100, the blood cell counter 110, the syllectogram measuring section 120, the blood discharge section 130, the operation and input section 140, the data output section 150, and the power supply section 160 are connected to the controller 170, and controlled by the controller 170. The syllectogram measuring section 120 and the controller 170 constitute the inflammatory marker measuring section.

The blood introducing section 100 obtains a blood specimen from a blood sampling tube which is set in an introduction port (not shown) of the inflammatory marker measurement apparatus 10 by a user such as a medical person, and then distributes the acquired blood specimen to the blood cell counter 110 and the syllectogram measuring section 120. The blood introducing section 100 has a dispensing section 101, a first pipe 102, a first suction pump 103, an electromagnetic valve 104, and a nozzle 105.

The dispensing section 101 is connected to the first suction pump 103 and the nozzle 105 through the first pipe 102. A supply port for supplying a diluent for diluting the blood specimen through the nozzle 105 is disposed in one end portion of the first pipe 102.

The blood specimen is previously collected from a patient, and accommodated in the blood sampling tube. As an anticoagulant, for example, ethylenediaminetetraacetic acid (EDTA) may be added to the blood specimen in the blood sampling tube.

The dispensing section 101 includes a movement mechanism which is not shown. The movement mechanism can move the nozzle 105 in the X, Y, and Z directions of the orthogonal coordinate system, and transfer the nozzle 105 from a position above the blood sampling tube in vertically upward and downward directions (the Z direction). The movement mechanism can further move the nozzle 105 in a horizontal direction (the X and Y directions). The movement mechanism transfers the nozzle 105 to predetermined positions above the blood cell counter 110 and the syllectogram measuring section 120. The predetermined positions are positions where the nozzle 105 can adequately inject the blood specimen into the blood cell counter 110 or the syllectogram measuring section 120.

The blood specimen in the blood sampling tube is caused by controlling the electromagnetic valve 104 to be sucked by the first suction pump 103 through the nozzle 105, and then held in the nozzle 105. The nozzle 105 is transferred to the predetermined positions above the blood cell counter 110 and the syllectogram measuring section 120, and, in each of the predetermined positions, injects a predetermined amount of the blood specimen into the blood cell counting or measuring section 110 or the syllectogram measuring section 120.

The dispensing section 101 may further include a specimen accommodating section which accommodates the blood specimen sucked from the blood sampling tube, and which is not shown. In this case, the blood specimen in the blood sampling tube is sucked by the first suction pump 103, and then accommodated in the specimen accommodating section through the nozzle 105. At this time, the electromagnetic valve 104 is controlled so that the blood specimen flows from the blood sampling tube into the specimen accommodating section.

The blood cell counter 110 has a first measuring unit 111 and a second measuring unit 112. Each of the first and second measuring units 111, 112 has a chamber and a detector. The chambers hold the blood specimen injected from the nozzle 105. The detectors measure the blood cell count in the blood specimen.

The blood specimen is injected into the chamber of the first measuring unit 111, diluted 200 times with the diluent, and hemolyzed with a hemolytic agent. Thereafter, the leukocyte count and the like are measured by the detector. The blood specimen is injected also into the chamber of the second measuring unit 112, and diluted 40.000 times with the diluent. The erythrocyte count and the like are measured by the detector. Each of the chambers is connected to the blood discharge section 130. When openable and closable electromagnetic valves v are opened, spent blood specimens are discharged into the blood discharge section 130.

The measurement items of the blood cell count include, for example, the leukocyte count (WBC), the erythrocyte count (RBC), the hemoglobin concentration (HGB), the hematocrit value (HCT), the mean corpuscular volume (MCV), the mean corpuscular hemoglobin (MCH), the mean corpuscular hemoglobin concentration (MCHC), the platelet count (PLT), the lymphocyte percentage (LY %), the monocyte percentage (MO %), the granulocyte percentage (GR %), the lymphocyte (LY), the monocyte (MO), and the granulocyte (GR), but are not limited to these items. Among the measurement items, for example, the blood cell count and the blood cell size are measured by the electrical resistivity method. The HGB is measured based on the principle of the colorimetric method. The HCT is measured from blood cell pulses by the cumulative pulse height method (calculated from an RBC histogram). These techniques for measuring a blood cell count are known, and therefore their description is omitted. The measurement data of the blood cell counts are sent to the controller 170.

The syllectogram measuring section 120 has a chamber 121, a transparent pipe 122, a transmission light detector 123, a second pipe 124, and a second suction pump 125. The syllectogram measuring section 120 measures the syllectogram of the blood specimen. The syllectogram is a graph showing the intensity transition of light transmitted through the blood specimen, the transition occurring, when the flow of the blood specimen caused by applying a shear stress to the blood specimen is stopped, across the stoppage.

The chamber 121 is configured to receive the blood specimen injected through the nozzle 105.

The transparent pipe 122 is, for example, a transparent glass tube. The lower end of the transparent pipe 122 communicates with the chamber 121, and the upper end is connected to a third pipe 132 through the second pipe 124. When suction is applied to the interior of the transparent pipe 122 by the second suction pump 125, a constant level of shear stress is applied to the blood specimen in the chamber 121. Since a shear stress is applied, the blood specimen flows through the transparent pipe 122 at a constant flow rate. Thereafter, the flow of the blood specimen is stopped by stoppage of the second suction pump 125, or switching or shutting off of an electromagnetic valve (not shown) which is disposed between the transmission light detector 123 and the second suction pump 125.

The transmission light detector 123 has a light source and a light detector. The light source illuminates the blood specimen in the transparent pipe 122 with light. The light detector detects the intensity of transmission light which is part of the illumination light illuminating the blood specimen, and which has been transmitted through the blood specimen (hereinafter, such an intensity will be referred to as "transmission light intensity"). The light source can be configured by, for example, a near-infrared generator. The light detector can be configured by a photodiode.

The transmission light detector 123 is configured to detect the transmission light intensity across the stoppage of the flow of the blood specimen which flows through the transparent pipe 122, and to send the sensing result to the controller 170. In other words, the transmission light detector 123 is configured to measure a syllectogram, and to send it to the controller 170.

The syllectogram measuring section 120 is adjusted by a heater or the like so that the temperature of the blood during the measurement is constant.

Figure 4:
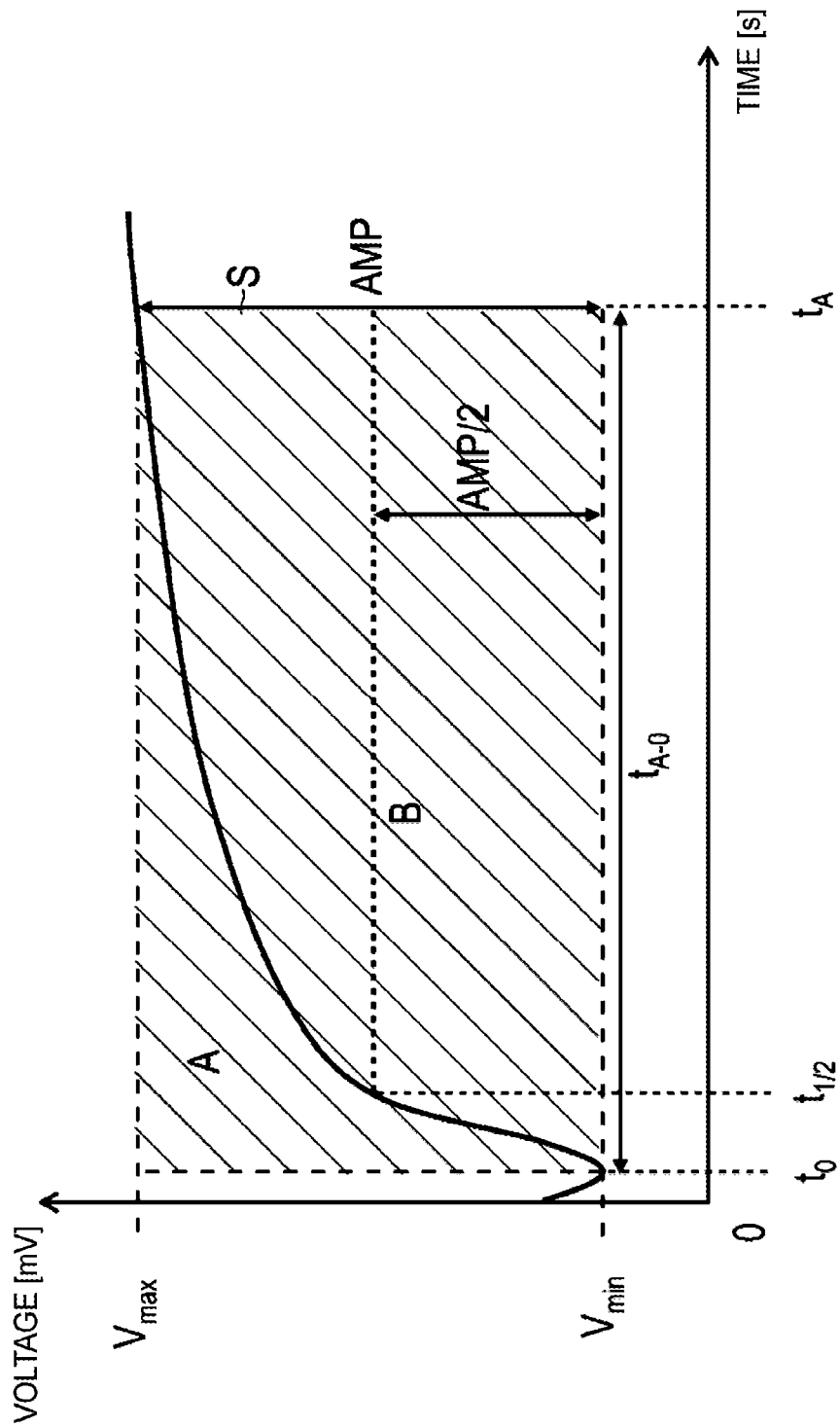
FIG. 4 illustrates an example of a syllectogram.

FIG. 4 illustrates an example of a syllectogram.

The abscissa of a syllectogram indicates the time, and the ordinate indicates the transmission light intensity. In the example of a syllectogram shown in FIG. 4, an output voltage of a photodiode which is used as the light detector of the transmission light detector 123 is indicated as the transmission light intensity.

In the syllectogram, the transmission light intensity has the minimum value $V_{min}$ at time $t_0$ when the flow of the blood specimen flowing through the transparent pipe 122 is stopped. This is caused by the phenomenon that, at the moment when the flow is stopped, erythrocytes hardly aggregate, and therefore the illumination light is reflected and absorbed by erythrocytes which are uniformly dispersed in the transparent pipe 122, whereby the transmission light intensity is reduced. After the transmission light intensity has the minimum value $V_{min}$ at time $t_0$, the intensity is increased. This is caused by the phenomenon that, when the flow is stopped, erythrocytes begin to aggregate, and the illumination light is transmitted through gaps which are between erythrocytes, and which are being increased in size by aggregation. The aggregation of erythrocytes occurs because repulsion between negatively charged erythrocytes is impeded by a blood protein such as fibrinogen which is increased by inflammation, and which is positively charged.

A parameter associated with aggregation (hereinafter, "aggregation parameter") is calculated based on the syllectogram. Examples of the aggregation parameter include a variety of parameters associated with the erythrocyte aggregation.

To calculate the aggregation parameter, time $t_A$ after a given period of time from time $t_0$ is set. This given period of time may be set based on a time at which, in the syllectogram, the increasing rate of the transmission light intensity is reduced by a certain degree to saturate. The transmission light intensity at time $t_A$ is set as the maximum value $V_{max}$ of the transmission light intensity in calculation of the aggregation parameter. The aggregation parameter can include a parameter AI calculated in the following manner based on the syllectogram. The parameter AI is calculated as a proportion of an area of region B to an area of region S in the syllectogram, the region S being a rectangle having one side defined by the time interval $t_A$) and another side defined by the difference AMP between the maximum value $V_{max}$ and the minimum value $V_{min}$ of the transmission light intensity, and the region B being a portion of the region S below the curve of the syllectogram. In FIG. 4, the region S is indicated by hatching. In other words, in the syllectogram, the parameter AI is calculated as the proportion of the area of the region B to the sum of the area of the region A and the area of the region B (i.e., B/(A+B)), the region A being a portion of the region S above the curve of the syllectogram. The aggregation parameter may include, in addition to the parameter AI, the values of the area of the region B, that of the region A, the difference AMP, and a time $t_{1/2}$. The time $t_{1/2}$ is a time when the transmission light intensity is increased by the half of the difference AMP/2 from the minimum value $V_{min}$ of the transmission light intensity at time $t_0$.

The blood discharge section 130 has the second suction pump 125, a discharge tank 131, the third pipe 132. As described above, the second suction pump 125 functions also as a component of the syllectogram measuring section 120. The second suction pump 125 sucks spent blood specimens from the blood cell counter 110 and the syllectogram measuring section 120. The discharge tank 131 reserves the spent blood specimens which are sucked by the second suction pump 125. A third suction pump for the ESR measurement may be added and used in parallel.

The operation and input section 140 is, for example, a touch panel, and is configured to receive instructions and data input by a user such as a medical person. Instructions by the user may include an instruction for measuring the ESR and an instruction for measuring the blood cell count. The input data may include a function for calculating the ESR. The function for calculating the ESR is a nonlinear function according to which the ESR is calculated based on the aggregation parameter and a parameter associated with the erythrocyte density. The parameter associated with the erythrocyte density may be at least one of, for example, the HCT, the RBC, the HGB, and the intensity transition of light transmitted through the blood specimen.

The data output section 150 is configured to output measurement data including the blood cell count and the ESR, various setting menus, various operation menus, and messages. The "output" may be, for example, an output in the form of a data signal, an output of sheets on which data are printed, and/or a display on a screen of a display device. The data output section 150 includes a data transmission-reception connector, a printer, and the display device.

In accordance with an instruction by the user, the data output section 150 may display both the measurement result of the blood cell count and the identification result of the ESR. In particular, the simultaneous display of the HCT with the ESR urges the user to consider the HCT when evaluating the measured ESR, and whereby the screening is facilitated. In addition to the HCT, the HGB, leukocytes, and the like may also be displayed together with the ESR, allowing the user to easily perform a screening of anemia or a disease that involves inflammation.

The HCT measured by the blood cell counter, and the HCT estimated from the transmission light intensity obtained from the syllectogram measuring section 120 are compared to each other, and a message suggesting that there is a possibility that the ESR is not adequately measured can be displayed on the data output section 150.

The power supply section 160 supplies necessary electric power to the blood introducing section 100, the blood cell counter 110, the syllectogram measuring section 120, the blood discharge section 130, the operation and input section 140, the data output section 150, and the controller 170.

The controller 170 controls the blood introducing section 100, the blood cell counter 110, the syllectogram measuring section 120, the blood discharge section 130, the operation and input section 140, the data output section 150, and the power supply section 160, and receives necessary data from the sections.

As shown in FIG. 3, the controller 170 has a central processing unit (CPU) 171, a random access memory (RAM) 172, a read only memory (ROM) 173, and a hard disk drive (HDD) 174. These components are connected to one another so as to be communicable with one another through a bus 175.

The CPU 171 is a processor which controls the components of the controller 170 in accordance with programs, and which performs various calculations. The CPU 171 executes an inflammatory marker measurement program P stored in the HDD 174, thereby measuring the ESR.

The RAM 172 is a volatile storage device, and temporarily stores the inflammatory marker measurement program P, measurement data, and functions which will be described later, and which are used for calculating the ESR.

The ROM 173 is a non-volatile storage device, and stores various data including setting data which will be used in execution of the inflammatory marker measurement program P.

The HDD 174 stores an operating system, various programs including the inflammatory marker measurement program P, and various data including measurement data, the functions for calculating the ESR, and basic information of the patient. The basic information of the patient includes the ID, name, and age of the patient. A label onto which the ID of the patient is printed is attached to the blood sampling tube, and the blood sampling tube and the measurement data can be managed by using the ID of the patient.

The functions (regression formulae) for calculating the ESR will be described.

Figure 5:
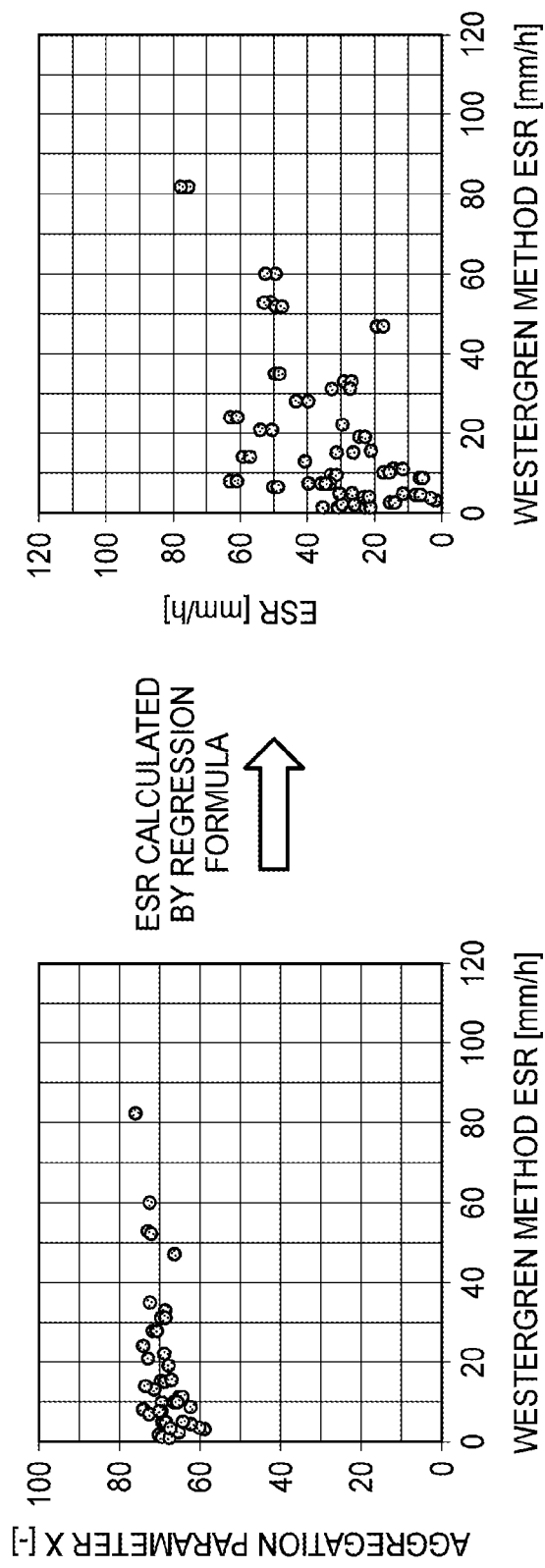
FIG. 5 illustrates a distribution chart showing a relationship between an ESR measured by the Westergren method and an aggregation parameter, and a distribution chart showing a relationship between the ESR measured by the Westergren method and an ESR calculated by a regression formula including the aggregation parameter as a variable.

FIG. 5 illustrates a distribution chart showing a relationship between an ESR measured by the Westergren method and the aggregation parameter, and a distribution chart showing a relationship between the ESR measured by the Westergren method and an ESR calculated by a regression formula including the aggregation parameter as a variable. In the following, an example in which the aggregation parameter X is the parameter AI will be described. The ESR measured by the Westergren method will be referred to as "the reference method ESR".

A nonlinear regression formula which is used for calculating the ESR while using the aggregation parameter X as a variable is produced, and the ESR which is calculated by substituting values of the aggregation parameter X that are plotted in the left distribution chart of FIG. 5, into the regression formula, and the reference method ESR are compared to each other. The comparison can be performed by, as shown in the right distribution chart of FIG. 5, plotting relationships between the reference method ESR and the ESR calculated by the regression formula. The regression formula may be formed as a nonlinear formula (for example, an exponential function or a power function) in which a square sum of deviations with respect to the reference method ESR is made minimum by the least square method.

As seen from the right distribution chart of FIG. 5, the ESR that is calculated by the regression formula in which only the aggregation parameter X based on the syllectogram is used as a variable does not have good correlation with the reference method ESR. Even when the ESR is calculated by a regression formula in which only the aggregation parameter X is used as a variable, therefore, the deviation from the reference method ESR cannot be sufficiently reduced.

Figure 6:
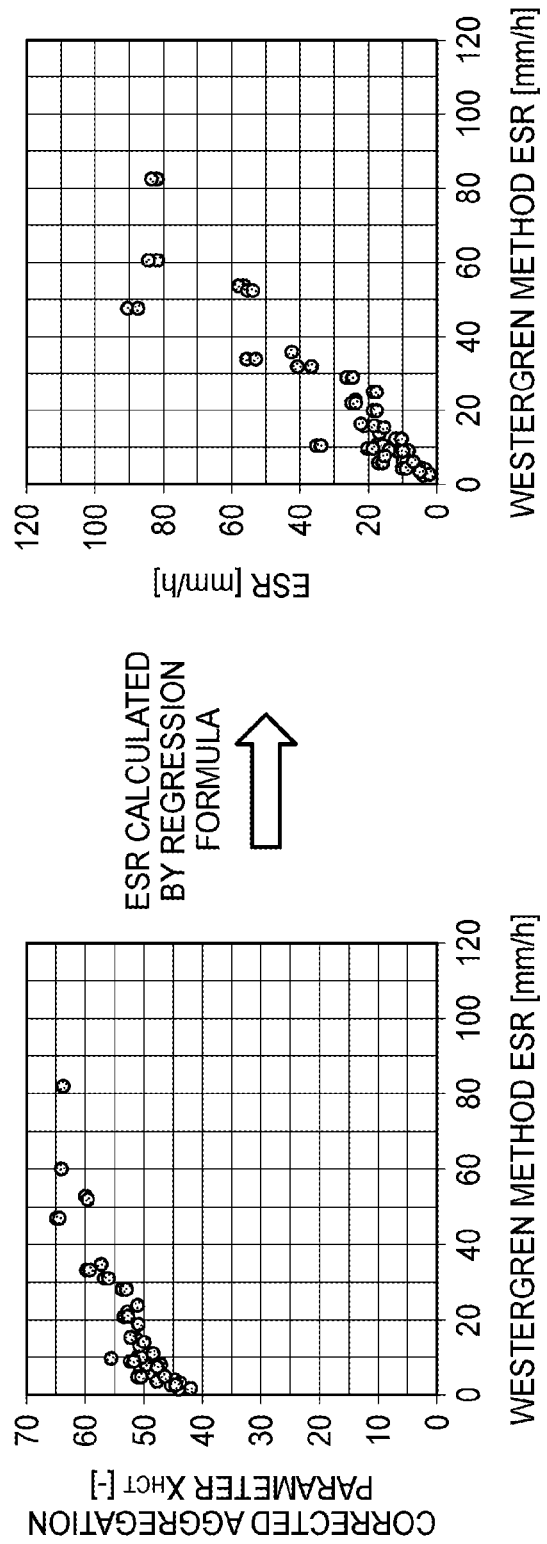
FIG. 6 illustrates a distribution chart showing a relationship between an ESR measured by the Westergren method and an aggregation parameter corrected by a hematocrit value, and a distribution chart showing a relationship between the ESR measured by the Westergren method and an ESR calculated by a regression formula including the aggregation parameter and the hematocrit value as variables.

FIG. 6 illustrates a distribution chart showing a relationship between the reference method ESR, and an aggregation parameter corrected by the HCT, and a distribution chart showing a relationship between the reference method ESR, and the ESR calculated by a regression formula in which the aggregation parameter and the HCT are used as variables.

Depending on a parameter associated with the erythrocyte density, also the aggregation parameter X is changed. When the HCT which is a parameter associated with the erythrocyte density is increased, for example, also the aggregation parameter X is increased. Therefore, correction is performed by dividing the aggregation parameter X by the HCT. Namely, the corrected aggregation parameter $X_{HCT}$ is set as aX/HCT (a being a constant optimized by experiments, X being the aggregation parameter, and HCT being the hematocrit value). A nonlinear regression formula which is used for calculating the ESR while using the corrected aggregation parameter $X_{HCT}$ as a variable is produced, and ESRs which are calculated by substituting the values of the corrected aggregation parameters $X_{HCT}$ plotted in the left distribution chart of FIG. 6, into the regression formula are compared with the reference method ESR. The comparison can be performed by, as shown in the right distribution chart of FIG. 6, plotting relationships of the reference method ESR and the ESR calculated by the regression formula, in a distribution chart. The correction of the aggregation parameter X is requested to be correction in which the aggregation parameter X is reduced in accordance with increase of the HCT, and may be, for example, correction in which the HCT (or a value that is obtained by multiplying the HCT by a constant) is subtracted from the aggregation parameter X. The above-described regression formula in which the corrected aggregation parameter $X_{HCT}$ is used as a variable uses the aggregation parameter $X_{HCT}$ that is corrected by the HCT, as a variable. Therefore, the regression formula can be said also as a regression formula in which the aggregation parameter X and the HCT are used as variables. The regression formula may be formed as a nonlinear formula (for example, an exponential function or a power function) in which a square sum of deviations with respect to the reference method ESR is made minimum by the least square method.

As described above, the parameter associated with the erythrocyte density includes the HCT, the RBC, the HGB, and the intensity transition of light transmitted through the blood specimen. Therefore, the aggregation parameter X can be corrected based on at least one of the HCT, the RBC, the HGB, and the intensity of light transmitted through the blood specimen. Based on at least one of the HCT, the RBC, the HGB, and the intensity transition of light transmitted through the blood specimen, namely, correction in which influences of these parameters are eliminated can be performed on the aggregation parameter X.

As seen from the right distribution chart of FIG. 6, the ESR that is calculated by the nonlinear regression formula in which the aggregation parameter X and the HCT are used as variables has good correlation with the reference method ESR. Therefore, it is seen that, when the ESR is calculated by a nonlinear regression formula in which the aggregation parameter X and the HCT are used as variables, the deviation from the reference method ESR can be reduced. Consequently, the regression formula can be used as the function for calculating the ESR.

Figure 7:
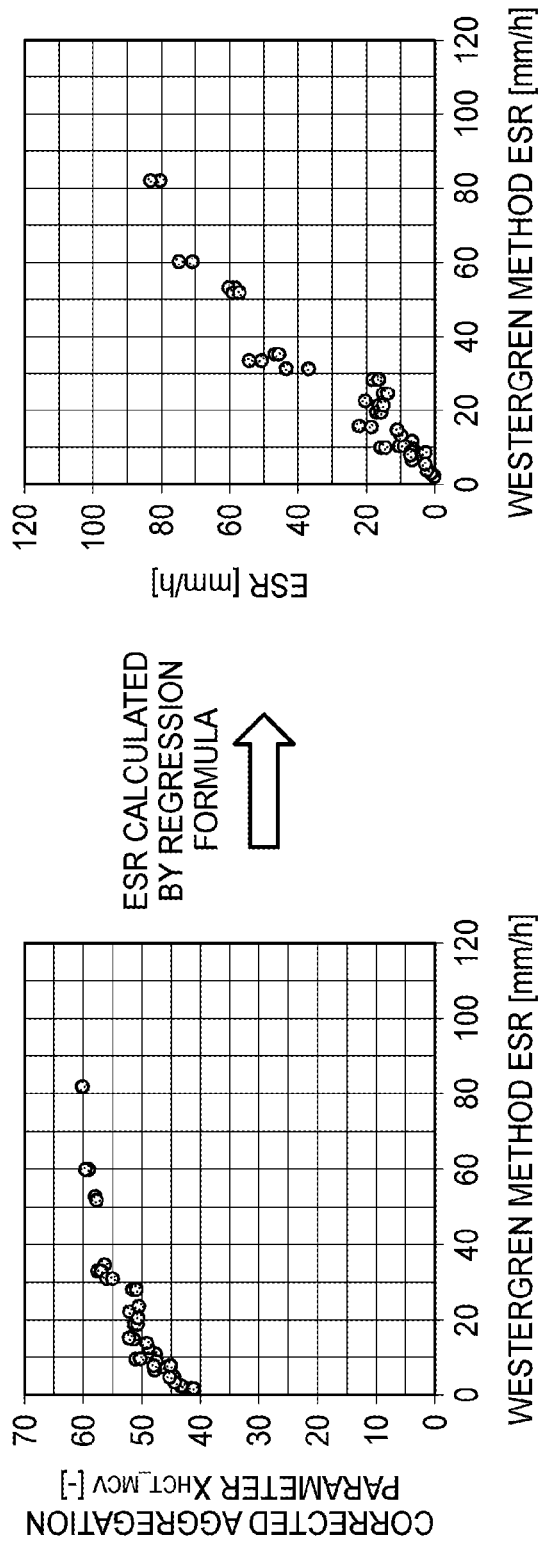
FIG. 7 illustrates a distribution chart showing a relationship between an ESR measured by the Westergren method and an aggregation parameter corrected by a hematocrit value and a mean corpuscular volume, and a distribution chart showing a relationship between the ESR measured by the Westergren method and an ESR calculated by a regression formula including the aggregation parameter, the hematocrit value, and the mean corpuscular volume as variables.

FIG. 7 illustrates a distribution chart showing a relationship between the reference method ESR, and an aggregation parameter corrected by the HCT and the mean corpuscular volume, and a distribution chart showing a relationship between the reference method ESR, and the ESR calculated by a regression formula in which the aggregation parameter, the HCT, and the mean corpuscular volume are used as variables.

According to the Stokes formula, the ESR is increased in proportion to the square of the diameter of an RBC aggregate. Therefore, the ESR is affected by a parameter associated with the erythrocyte volume. Therefore, the aggregation parameter $X_{HCT}$ which is corrected by the HCT is further corrected by the mean corpuscular volume (MCV). The parameter associated with the erythrocyte volume includes at least one of the mean corpuscular volume (MCV), the mean corpuscular hemoglobin (MCH), the mean corpuscular hemoglobin concentration (MCHC), and the HGB. In the following, an example in which the parameter associated with the erythrocyte volume is the mean corpuscular volume will be described. Since the volume of a sphere is $4/3[pi]r^3$ (r being the radius of the sphere), it is considered that the ESR is proportional to the two-third power of the mean corpuscular volume. However, erythrocytes do not have a perfect spherical shape. Therefore, the corrected aggregation parameter $X_{HCT\_MCV}$ is set as $X_{HCT} MCV^b$ (b being a constant optimized by experiments, $X_{HCT}$ being the aggregation parameter corrected by the HCT, and MCV being the mean corpuscular volume). Then, a nonlinear regression formula which is used for calculating the ESR while using the corrected aggregation parameter $X_{HCT\_MCV}$ as a variable is produced, and ESRs which are calculated by substituting the values of the corrected aggregation parameter $X_{HCT\_MCV}$ plotted in the left distribution chart of FIG. 7, into the regression formula are compared with the reference method ESR. The comparison can be performed by, as shown in the right distribution chart of FIG. 7, plotting relationships of the reference method ESR and the ESRs calculated by the regression formula, in a distribution chart. The above-described regression formula in which the corrected aggregation parameter $X_{HCT\_MCV}$ is used as a variable uses the aggregation parameter $X_{HCT\_MCV}$ that is corrected by the HCT and further corrected by the mean corpuscular volume, as a variable. Therefore, the regression formula can be said also as a regression formula in which the aggregation parameter, the HCT, and the mean corpuscular volume are used as variables. The regression formula may be formed as a nonlinear formula (for example, an exponential function or a power function) in which a square sum of deviations with respect to the reference method ESR is made minimum by the least square method.

As seen from the right distribution chart of FIG. 7, the ESR that is calculated by the regression formula in which the aggregation parameter X, the HCT, and the mean corpuscular volume are used as variables has better correlation with the reference method ESR. Therefore, it is seen that, when the ESR is calculated by a regression formula in which the aggregation parameter X, the HCT, and the mean corpuscular volume are used as variables, the deviation from the reference method ESR can be further reduced. Consequently, the regression formula can be used as the function for calculating the ESR.

As described above, the function for calculating the ESR is a nonlinear regression formula in which the aggregation parameter and the HCT are used as variables, or a nonlinear regression formula in which the aggregation parameter, the HCT, and the mean corpuscular volume are used as variables. The fitting which is to be performed by the least square method with respect to the reference method ESR in obtaining the regression formula must be conducted by using a nonlinear function in which the corrected aggregation parameter that is corrected by the HCT (or the HCT and the mean corpuscular volume) is used as a variable. This is because a nonlinear function is employed in a regression formula which is used in the fitting with respect to the reference method ESR, and therefore, even when correction using the HCT or the like is performed on a regression formula after fitting, a correct ESR cannot be calculated.

Figure 8:
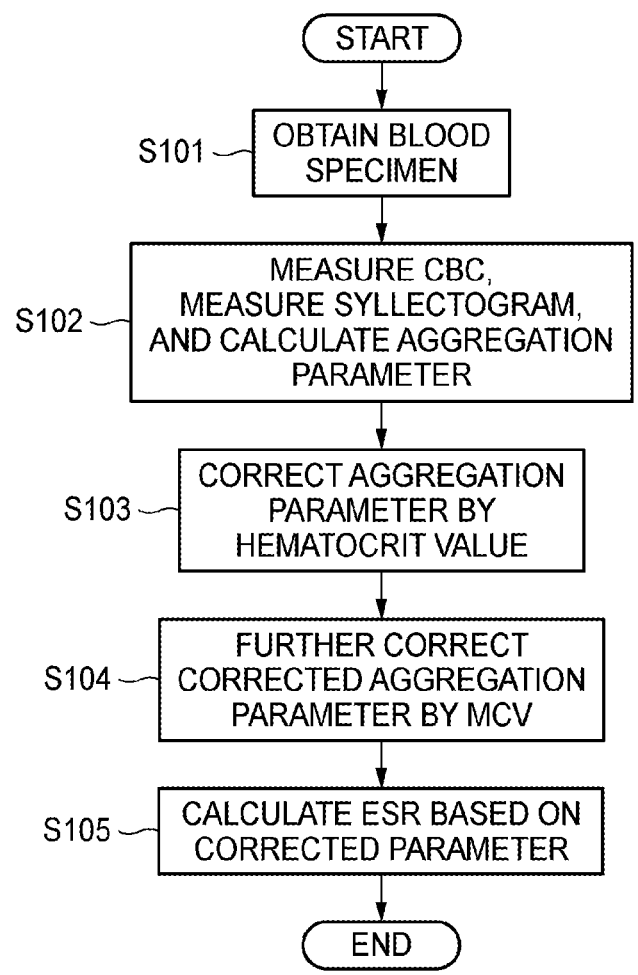
FIG. 8 is a flowchart of a method for measuring an ESR.

FIG. 8 is a flowchart of a method of measuring an ESR. The flowchart can be executed by the controller 170 in accordance with the inflammatory marker measurement program P.

The controller 170 is configured to cause the blood introducing section 100 to obtain a blood specimen from the blood sampling tube, and to supply the blood specimen to the blood cell counter 110 and the syllectogram measuring section 120 (S101). This step is initiated based on an instruction input by a user such as a medical person through the operation and input section 140. In the following, an example in which an ESR measurement is instructed by a user will be described. As described above, the ESR measurement is executed by a calculation based on the aggregation parameters, the parameter associated with the erythrocyte density, and a measurement value of at least one of the mean corpuscular volume, the mean corpuscular hemoglobin, the mean corpuscular hemoglobin concentration, and the HGB. Thus, even when the user instructs only the ESR measurement to be performed, the measurement of the blood cell count can be performed in parallel.

The controller 170 causes the blood cell counter 110 to measure the blood cell count, causes the syllectogram measuring section 120 to measure the syllectogram, and calculates the aggregation parameter (S102).

The controller 170 corrects the aggregation parameter calculated in step S102, by using the HCT (S103).

The controller 170 further corrects the aggregation parameter which is corrected in step S103, by using the mean corpuscular volume (S104).

The controller 170 calculates the ESR based on the aggregation parameter which is corrected in step S104 (S105).

The procedures in steps S103 to S105 are equivalent to the procedure for calculating the ESR based on the aggregation parameter, the parameter associated with the erythrocyte density, and a measurement value of the mean corpuscular volume. Namely, the procedures are equivalent to the procedure for calculating the ESR by substituting the aggregation parameter, the parameter associated with the erythrocyte density, and the mean corpuscular volume for variables of a function for calculating the ESR. Therefore, the procedures in steps S103 to S105 can be executed substantially simultaneously.

The embodiment achieves the following effects.

The ESR is calculated by using a nonlinear function having a parameter associated with the erythrocyte aggregation based on a measured syllectogram and a parameter associated with the measured erythrocyte density as variables. According to this configuration, an ESR measurement in which the deviation from a value measured by the reference method is reduced can be realized in a short period of time.

Moreover, at least one of the mean corpuscular volume, the mean corpuscular hemoglobin, the mean corpuscular hemoglobin concentration, and the HGB is additionally used as a variable of the function. According to the configuration, the deviation from the value measured by the reference method can be further reduced.

Furthermore, the parameter associated with the erythrocyte density is at least one of the HCT, the RBC, the HGB, and the intensity of light transmitted through the blood specimen. According to the configuration, an ESR in which the deviation from a value measured by the reference method is reduced can be measured more simply and flexibly in accordance with the measurement item and the measurement environment.

Another embodiment of the presently disclosed subject matter will be described. This embodiment is different from the foregoing embodiment in that, the fibrinogen concentration is measured as an inflammatory marker by using a nonlinear function having the aggregation parameter and a parameter associated with the erythrocyte density as variables. Other features are the same or similar to the foregoing embodiment, and therefore description thereof will be omitted.

As described above, fibrinogen is a positively charged blood protein which is increased in accordance with inflammation. Repulsion between negatively charged erythrocytes is impeded by positively charged fibrinogen. When the fibrinogen concentration is increased, therefore, erythrocyte aggregation becomes remarkable.

The fibrinogen concentration is measured by calculating the fibrinogen concentration by using a nonlinear function in which the aggregation parameter and a parameter associated with the erythrocyte density are used as variables. In the nonlinear function, at least one of the MCV, the MCH, the MCHC, and the HGB can be used as a further variable.

A function (regression formula) for calculating the fibrinogen concentration will be described. The fibrinogen concentration is usually measured by the Clauss method (thrombin time method).

Figure 9:
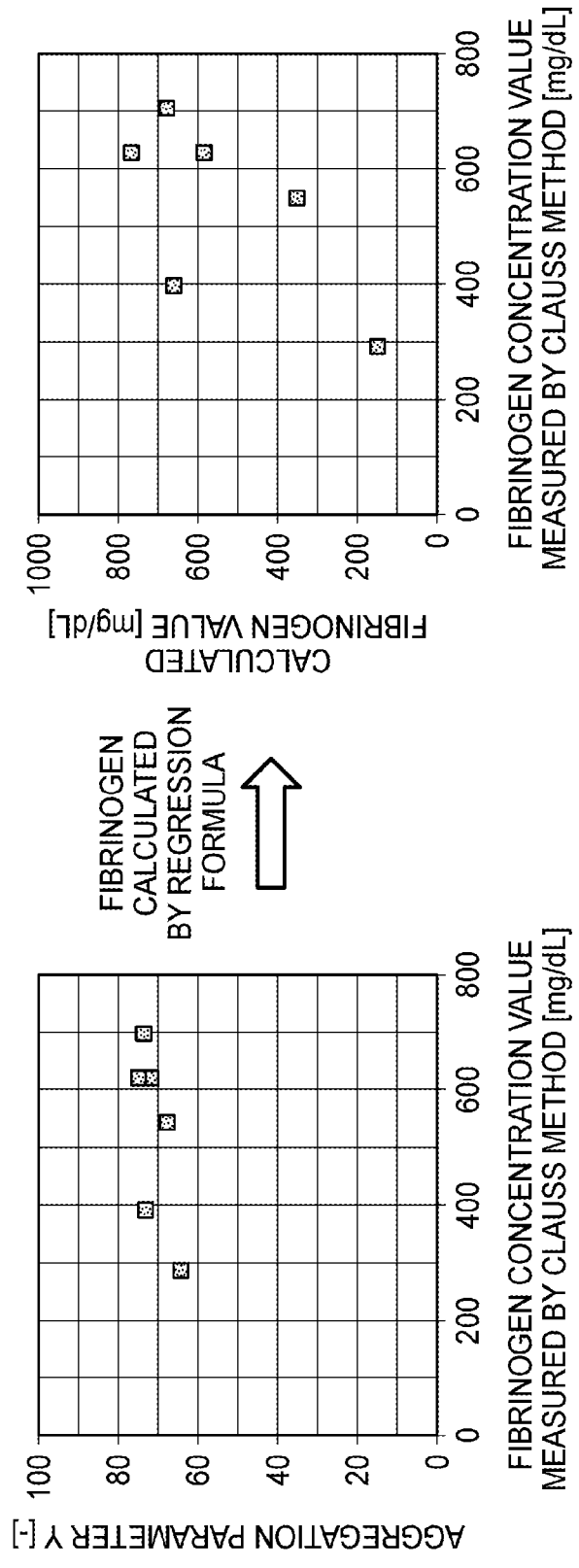
FIG. 9 illustrates a distribution chart showing a relationship between a fibrinogen concentration measured by the Clauss method and an aggregation parameter, and a distribution chart showing a relationship between the fibrinogen concentration measured by the Clauss method and a fibrinogen concentration calculated by a regression formula including the aggregation parameter as a variable.

FIG. 9 illustrates a distribution chart showing a relationship between a fibrinogen concentration measured by the Clauss method, and the aggregation parameter, and a distribution chart showing a relationship between the fibrinogen concentration measured by the Clauss method, and a fibrinogen concentration calculated by a regression formula having the aggregation parameter as a variable. In the following, an example in which the aggregation parameter Y is the parameter AI will be described. The fibrinogen concentration measured by the Clauss method will hereinafter be referred to as "the Clauss method fibrinogen concentration".

A regression formula used for calculating the fibrinogen concentration while using the aggregation parameter Y as a variable is produced from the relationship between the Clauss method fibrinogen concentration and the aggregation parameter Y, shown in the left distribution chart of FIG. 9. Then, the fibrinogen concentration calculated by substituting values of the aggregation parameter Y that are plotted in the left distribution chart of FIG. 9 into the produced regression formula, and the Clauss method fibrinogen concentration are compared to each other. The comparison can be performed by, as shown in the right distribution chart of FIG. 9, plotting relationships between the Clauss method fibrinogen concentration and the fibrinogen concentration calculated by the regression formula. The regression formula may be formed as a nonlinear formula (for example, a linear function, an exponential function, or a power function) in which a square sum of deviations with respect to the Clauss method fibrinogen concentration is made minimum by the least square method.

As seen from the right distribution chart of FIG. 9, the fibrinogen concentration that is calculated by the regression formula in which only the aggregation parameter Y based on the syllectogram is used as a variable does not have good correlation with the Clauss method fibrinogen concentration. Even when the fibrinogen concentration is calculated by a regression formula in which only the aggregation parameter Y is used as a variable, therefore, the deviation from the Clauss method fibrinogen concentration is relatively large, and the fibrinogen concentration cannot be accurately measured.

Figure 10:
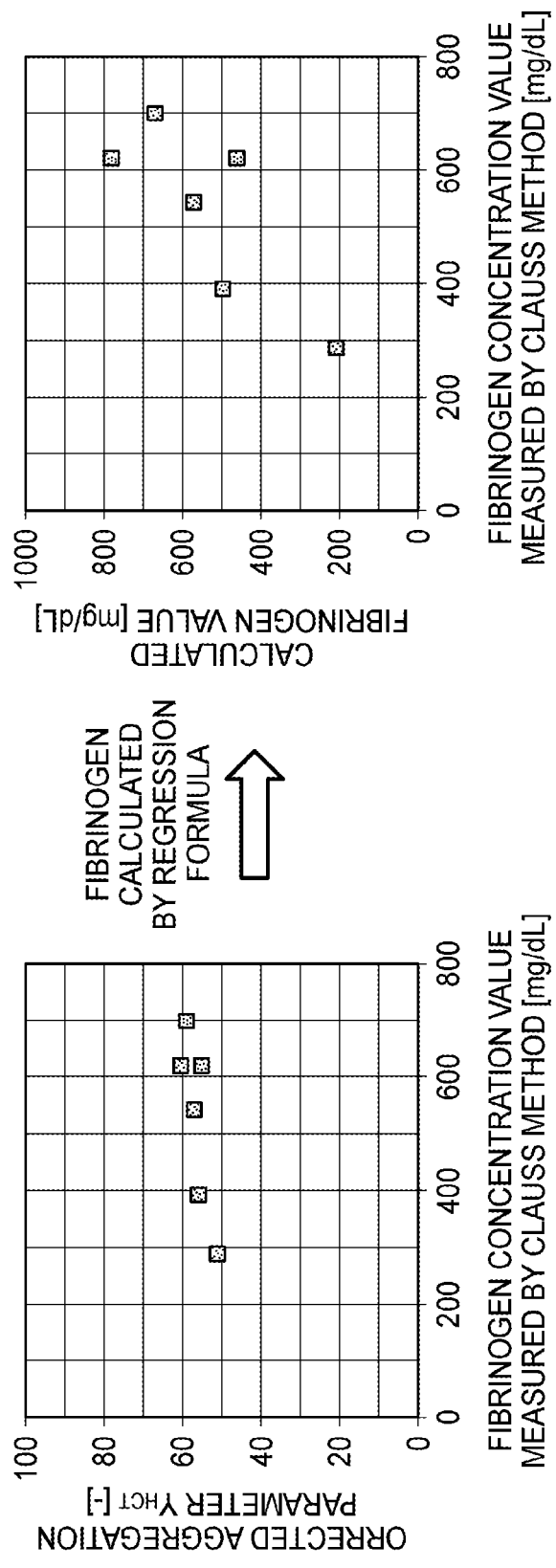
FIG. 10 illustrates a distribution chart showing a relationship between a fibrinogen concentration measured by the Clauss method and an aggregation parameter corrected by an HCT, and a distribution chart showing a relationship between the fibrinogen concentration measured by the Clauss method and a fibrinogen concentration calculated by a regression formula including the aggregation parameter and the HCT as variables.

FIG. 10 illustrates a distribution chart showing a relationship between the Clauss method fibrinogen concentration, and an aggregation parameter corrected by an HCT, and a distribution chart showing a relationship between the Clauss method fibrinogen concentration, and a fibrinogen concentration calculated by a regression formula in which the aggregation parameter and the HCT are used as variables.

Depending on a parameter associated with the erythrocyte density, also the aggregation parameter Y is changed. When the HCT which is a parameter associated with the erythrocyte density is increased, for example, also the aggregation parameter Y is increased. Therefore, correction is performed by subtracting the HCT (or a value which is obtained by multiplying the HCT by a constant) from the aggregation parameter Y. Namely, the corrected aggregation parameter $Y_{HCT}$ is set as Y-cHCT (c being a constant optimized by experiments, Y being the aggregation parameter, and HCT being the hematocrit value). A regression formula used for calculating the fibrinogen concentration while using the corrected aggregation parameter $Y_{HCT}$ as a variable is produced from the relationship between the Clauss method fibrinogen concentration and the corrected aggregation parameter $Y_{HCT}$, shown in the left distribution chart of FIG. 10. Then, the fibrinogen concentrations calculated by substituting the values of the corrected aggregation parameters $Y_{HCT}$ plotted in the left distribution chart of FIG. 10, in the produced regression formula are compared with the Clauss method fibrinogen concentration. The comparison can be performed by, as shown in the right distribution chart of FIG. 10, plotting relationships of the Clauss method fibrinogen concentration and the fibrinogen concentrations calculated by the regression formula, in a distribution chart. The correction of the aggregation parameter Y is requested to be correction in which the aggregation parameter Y is reduced in accordance with increase of the HCT, and may be, for example, correction in which the aggregation parameter Y is divided by the HCT (or a value that is obtained by multiplying the HCT by a constant). The above-described regression formula in which the corrected aggregation parameter $Y_{HCT}$ is used as a variable uses the aggregation parameter $Y_{HCT}$ that is corrected by the HCT, as a variable, and therefore can be said also as a regression formula in which the aggregation parameter Y and the HCT are used as variables. The regression formula may be formed as a nonlinear formula (for example, an exponential function or a power function) in which a square sum of deviations with respect to the Clauss method fibrinogen concentration is made minimum by the least square method.

As described above, the parameter associated with the erythrocyte density includes the HCT, the RBC, the HGB, and the intensity of light transmitted through the blood specimen. Therefore, the aggregation parameter Y can be corrected based on at least one of the HCT, the RBC, the HGB, and the intensity of light transmitted through the blood specimen. Based on at least one of the HCT, the RBC, the HGB, and the intensity transition of light transmitted through the blood specimen, namely, correction in which influences of these parameters are eliminated can be performed on the aggregation parameter Y.

As seen from the right distribution chart of FIG. 10, the fibrinogen concentration that is calculated by the regression formula in which the aggregation parameter Y and the HCT are used as variables has good correlation with the Clauss method fibrinogen concentration. Therefore, it is seen that, when the fibrinogen concentration is calculated by a nonlinear regression formula in which the aggregation parameter Y and the HCT are used as variables, the deviation from the Clauss method fibrinogen concentration can be reduced. Consequently, the regression formula can be used as the function for calculating the fibrinogen concentration.

Figure 11:
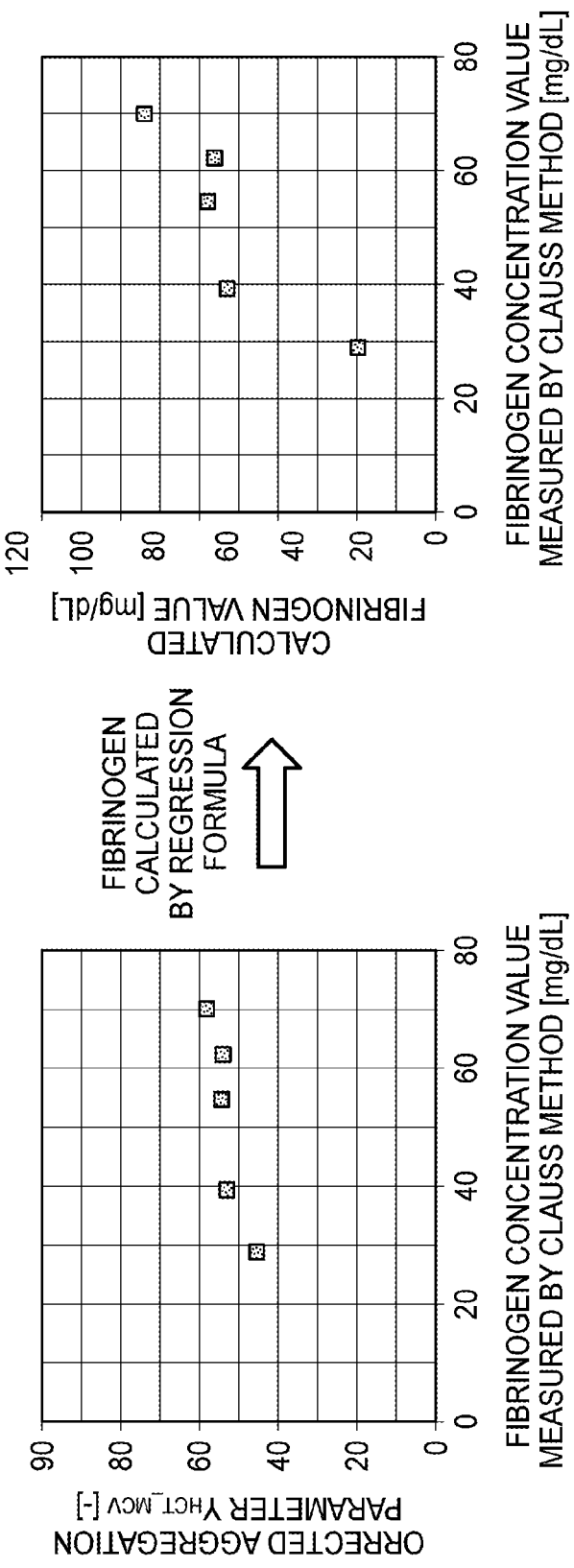
FIG. 11 illustrates a distribution chart showing a relationship between a fibrinogen concentration measured by the Clauss method and an aggregation parameter corrected by an HCT and a mean corpuscular volume, and a distribution chart showing a relationship between the fibrinogen concentration measured by the Clauss method and a fibrinogen concentration calculated by a regression formula including the aggregation parameter, the HCT, and the mean corpuscular volume as variables.

FIG. 11 illustrates a distribution chart showing a relationship between the Clauss method fibrinogen concentration, and an aggregation parameter corrected by an HCT and the mean corpuscular volume, and a distribution chart showing a relationship between the Clauss method fibrinogen concentration, and a fibrinogen concentration calculated by a regression formula in which the aggregation parameter, the HCT, and the mean corpuscular volume are used as variables.

The above-described Stokes formula is premised on erythrocyte sedimentation. Therefore, it is considered that the Stokes formula cannot be applied to the fibrinogen concentration which is not premised on erythrocyte sedimentation. However, erythrocyte aggregation is affected by the surface area and volume of an erythrocyte. Therefore, the corrected aggregation parameter $Y_{HCT\_MCV}$ is set as $dY_{HCT}MCV^e$ (d being a constant optimized by experiments, $Y_{HCT}$ being the aggregation parameter corrected by the HCT, MCV being the mean corpuscular volume, and e being a constant optimized by experiments).

A regression formula used for calculating the fibrinogen concentration while using the corrected aggregation parameter $Y_{HCT\_MCV}$ as a variable is produced from the relationship between the Clauss method fibrinogen concentration and the corrected aggregation parameter $Y_{HCT\_MCV}$, shown in the left distribution chart of FIG. 11. Then, the fibrinogen concentration calculated by substituting values of the corrected aggregation parameter $Y_{HCT\_MCV}$ that are plotted in the left distribution chart of FIG. 11 into the produced regression formula, and the Clauss method fibrinogen concentration are compared to each other. The comparison can be performed by, as shown in the right distribution chart of FIG. 11, plotting relationships between the Clauss method fibrinogen concentration and the fibrinogen concentration calculated by the regression formula. The above-described regression formula including the corrected aggregation parameter $Y_{HCT\_MCV}$ as a variable uses the aggregation parameter $Y_{HCT\_MCV}$ that is corrected by the HCT and further corrected by the mean corpuscular volume, as a variable. Therefore, the regression formula can be said also as a regression formula in which the aggregation parameter, the HCT, and the mean corpuscular volume are used as variables. The regression formula may be formed as a nonlinear formula (for example, an exponential function or a power function) in which a square sum of deviations with respect to the Clauss method fibrinogen concentration is made minimum by the least square method.

As seen from the right distribution chart of FIG. 11, the fibrinogen concentration that is calculated by the regression formula in which the aggregation parameter Y, the HCT, and the mean corpuscular volume are used as variables has better correlation with the Clauss method fibrinogen concentration. Therefore, it is seen that, when the fibrinogen concentration is calculated by a regression formula in which the aggregation parameter Y, the HCT, and the mean corpuscular volume are used as variables, the deviation from the Clauss method fibrinogen concentration can be further reduced. Consequently, the regression formula can be used as the function for calculating the fibrinogen concentration.

The function for calculating the fibrinogen concentration is a nonlinear regression formula in which the aggregation parameter Y and the HCT are used as variables, or a nonlinear regression formula in which the aggregation parameter Y, the HCT, and the mean corpuscular volume are used as variables. The fitting which is to be performed by the least square method with respect to the Clauss method fibrinogen concentration in obtaining the regression formula must be conducted by using a nonlinear function in which the corrected aggregation parameter that is corrected by the HCT (or the HCT and the mean corpuscular volume) is used as a variable. This is because a nonlinear function is employed in a regression formula which is used in the fitting with respect to the Clauss method fibrinogen concentration, and therefore, even when correction using the HCT or the like is performed on a regression formula after fitting, a correct fibrinogen concentration cannot be calculated.

Figure 12:
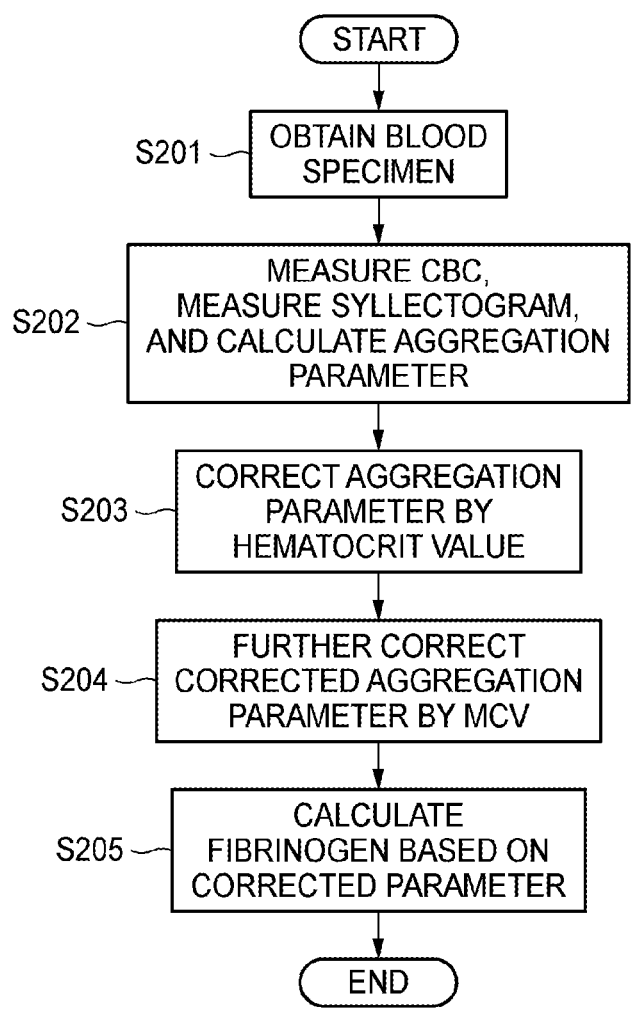
FIG. 12 is a flowchart of a method for measuring a fibrinogen concentration.

FIG. 12 is a flowchart of a method of measuring a fibrinogen concentration. The flowchart can be executed by the controller 170 in accordance with the inflammatory marker measurement program P.

The controller 170 is configured to cause the blood introducing section 100 to obtain a blood specimen from the blood sampling tube, and to supply the blood specimen to the blood cell counter 110 and the syllectogram measuring section 120 (S201). This step is initiated based on an instruction input by a user such as a medical person through the operation and input section 140. In the following, an example in which the fibrinogen concentration measurement is instructed by the user will be described. As described above, the fibrinogen concentration measurement is executed by a calculation based on the aggregation parameter, a parameter associated with the erythrocyte density, and a measurement value of at least one of the mean corpuscular volume, the mean corpuscular hemoglobin, the mean corpuscular hemoglobin concentration, and the HGB. Thus, even when the user instructs only the fibrinogen concentration measurement to be performed, the measurement of the blood cell count can be performed in parallel.

The controller 170 causes the blood cell counter 110 to measure the blood cell count, causes the syllectogram measuring section 120 to measure the syllectogram, and calculates the aggregation parameter (S202).

The controller 170 corrects the aggregation parameter calculated in step S202, by using the HCT (S203).

The controller 170 further corrects the aggregation parameter which is corrected in step S203, by using the mean corpuscular volume (S204).

The controller 170 calculates the fibrinogen concentration based on the aggregation parameter which is corrected in step S204 (S205).

The steps S203 to S205 are equivalent to the steps for calculating the fibrinogen concentration based on the aggregation parameter, the parameter associated with the erythrocyte density, and a measurement value of the mean corpuscular volume. That is, the steps are equivalent to the steps for calculating the fibrinogen concentration by substituting the aggregation parameter, the parameter associated with the erythrocyte density, and the mean corpuscular volume for variables of a function for calculating the fibrinogen concentration. Therefore, the steps S203 to S205 can be executed substantially simultaneously.

The embodiment achieves the following effects.

The fibrinogen concentration is calculated by using a nonlinear function including, as variables, a parameter associated with the erythrocyte aggregation based on a measured syllectogram, and another parameter associated with the measured erythrocyte density. According to this configuration, an accurate fibrinogen concentration measurement can be realized.

Moreover, at least one of the mean corpuscular volume, the mean corpuscular hemoglobin, the mean corpuscular hemoglobin concentration, and the HGB is additionally used as a variable of the function. According to the configuration, a more accurate fibrinogen concentration measurement can be realized.

Furthermore, the parameter associated with the erythrocyte density is at least one of the HCT, the RBC, the HGB, and the intensity of light transmitted through the blood specimen. According to the configuration, an accurate fibrinogen concentration measurement can be realized more simply and flexibly in accordance with the measurement item and the measurement environment.

While the inflammatory marker measurement method, the inflammatory marker measurement apparatus, the inflammatory marker measurement program, and the recording medium storing the program have been described with reference to certain embodiments of the presently disclosed subject matter, the presently disclosed subject matter is not limited the embodiments described above.

For example, in the foregoing embodiments, the first and second measuring units are provided in the blood cell counter. However, if only a measurement of an inflammatory marker is required, the first measuring unit that measures the blood cell count for leukocytes may be omitted.

A part of or all of the functions executed by a program in the foregoing embodiments may be executed by means of hardware such as electronic circuits.

This application is based on Japanese Patent Application No. 2017-13292 filed on Jan. 27, 2017 and Japanese Patent Application No. 2017-195393 filed on Oct. 5, 2017, the entire contents of which are incorporated herein by reference.

The invention claimed is:

1. An inflammatory marker measurement method comprising:
    calculating, by a processor, an inflammatory marker using a nonlinear regression formula including, as variables, a parameter associated with an erythrocyte aggregation and another parameter associated with an erythrocyte density, wherein:
    the parameter associated with the erythrocyte aggregation is calculated based on a syllectogram measured from a blood specimen, and the parameter associated with the erythrocyte density is measured from the blood specimen, the syllectogram being measured by detecting, by a detector, an intensity of transmission light transmitted through the blood specimen after stopping a flow of the blood specimen by applying a shear stress to the blood specimen, and transmitting by the detector an outcome indicative of the intensity to the processor,
    the inflammatory marker comprises an erythrocyte sedimentation rate or a fibrinogen concentration, and
    the nonlinear regression formula is obtained by at least a square method such that a square sum of deviations with respect to the erythrocyte sedimentation rate of a reference method is made minimum, or by at least a square method such that a square sum of deviations with respect to the fibrinogen concentration of a Clauss method is made minimum.

2. The inflammatory marker measurement method according to claim 1, wherein the nonlinear regression formula includes, as a further variable, at least one of a mean corpuscular volume, a mean corpuscular hemoglobin, a mean corpuscular hemoglobin concentration, and a hemoglobin concentration.

3. The inflammatory marker measurement method according to claim 1, wherein the parameter associated with the erythrocyte density comprises at least one of a hematocrit value, an erythrocyte count, a hemoglobin concentration, and the intensity of light transmitted through the blood specimen.

4. An inflammatory marker measurement apparatus comprising:
    a detector; and
    a processor configured to calculate an inflammatory marker using a nonlinear regression formula including, as variables, a parameter associated with an erythrocyte aggregation and another parameter associated with an erythrocyte density, wherein:
    the parameter associated with the erythrocyte aggregation is calculated based on a syllectogram measured from a blood specimen, and the parameter associated with the erythrocyte density is measured from the blood specimen, the detector configured to measure the syllectogram by detecting an intensity of transmission light transmitted through the blood specimen after stopping a flow of the blood specimen by applying a shear stress to the blood specimen, the detector further configured to transmit an outcome indicative of the intensity to the processor, the inflammatory marker comprises at least one of an erythrocyte sedimentation rate and a fibrinogen concentration, and the nonlinear regression formula is obtained by at least a square method such that a square sum of deviations with respect to the erythrocyte sedimentation rate of a reference method is made minimum, or by at least a square method such that a square sum of deviations with respect to the fibrinogen concentration of a Clauss method is made minimum.

5. The inflammatory marker measurement apparatus according to claim 4, wherein the nonlinear regression formula includes, as a further variable, at least one of a mean corpuscular volume, a mean corpuscular hemoglobin, a mean corpuscular hemoglobin concentration, and a hemoglobin concentration.

6. The inflammatory marker measurement apparatus according to claim 4, wherein the parameter associated with the erythrocyte density comprises at least one of a hematocrit value, an erythrocyte count, a hemoglobin concentration, and the intensity of light transmitted through the blood specimen.

7. A non-transitory computer-readable recording medium storing an inflammatory marker measurement program which causes a processor to execute a method comprising:
calculating an inflammatory marker using a nonlinear regression formula including, as variables, a parameter associated with an erythrocyte aggregation and another parameter associated with an erythrocyte density, wherein:
the parameter associated with the erythrocyte aggregation is calculated based on a syllectogram measured from a blood specimen, and the parameter associated with the erythrocyte density is measured from the blood specimen, the syllectogram measured by detecting, by a detector, an intensity of transmission light transmitted through the blood specimen after stopping a flow of the blood specimen by applying a shear stress to the blood specimen, and transmitting by the detector an outcome indicative of the intensity to the processor,
the inflammatory marker comprises at least one of an erythrocyte sedimentation rate and a fibrinogen concentration, and
the nonlinear regression formula is obtained by at least a square method such that a square sum of deviations with respect to the erythrocyte sedimentation rate of a reference method is made minimum, or by at least a square method such that a square sum of deviations with respect to the fibrinogen concentration of a Clauss method is made minimum.

8. The computer-readable recording medium according to claim 7, wherein the nonlinear regression formula includes, as a further variable, at least one of a mean corpuscular volume, a mean corpuscular hemoglobin, a mean corpuscular hemoglobin concentration, and a hemoglobin concentration.

9. The computer-readable recording medium according to claim 7, wherein the parameter associated with the erythrocyte density comprises at least one of a hematocrit value, an erythrocyte count, a hemoglobin concentration, and the intensity of light transmitted through the blood specimen.

10. The inflammatory marker measurement method according to claim 1, further comprising adjusting a rate of the intensity of transmission light by a predetermined degree to saturate after setting a predetermined period of time so as to calculate the parameter associated with the erythrocyte aggregation.

11. The inflammatory marker measurement method according to claim 1, further comprising:
controlling, by the processor, a valve to obtain the blood specimen;
transferring, by the processor, a nozzle to a predetermined position, the nozzle configured to hold the blood specimen; and
injecting a predetermined amount of the blood specimen from the nozzle at the predetermined position into a chamber to calculate the inflammatory marker.

12. The inflammatory marker measurement apparatus according to claim 4, wherein the processor is further configured to adjust a rate of the intensity of transmission light by a predetermined degree to saturate after setting a predetermined period of time so as to calculate the parameter associated with the erythrocyte aggregation.

13. The inflammatory marker measurement apparatus according to claim 4, further comprising:
a valve; and
a nozzle, wherein the processor is further configured to:
control the valve to obtain the blood specimen;
transfer the nozzle to a predetermined position, the nozzle configured to hold the blood specimen; and
inject a predetermined amount of the blood specimen from the nozzle at the predetermined position into a chamber to calculate the inflammatory marker.

14. The computer-readable recording medium according to claim 7, further comprising adjusting a rate of the intensity of transmission light by a predetermined degree to saturate after setting a predetermined period of time so as to calculate the parameter associated with the erythrocyte aggregation.

15. The computer-readable recording medium according to claim 7, further comprising:
controlling a valve to obtain the blood specimen;
transferring a nozzle to a predetermined position, the nozzle configured to hold the blood specimen; and
injecting a predetermined amount of the blood specimen from the nozzle at the predetermined position into a chamber to calculate the inflammatory marker.

* * * * *

UNITED STATES PATENT AND TRADEMARK OFFICE
CERTIFICATE OF CORRECTION

PATENT NO. : 11,555,773 B2
APPLICATION NO. : 16/469261
DATED : January 17, 2023
INVENTOR(S) : Makoto Higuchi It is certified that error appears in the above-identified patent and that said Letters Patent is hereby corrected as shown below:

In the Specification

Column 6, Line 31, "interval $t_A$) and another" should read -- interval $t_{A-0}$ and another --

Signed and Sealed this
Fifth Day of December, 2023

Katherine Kelly Vidal
*Director of the United States Patent and Trademark Office*